(12) United States Patent
Nakashima (10) Patent No.: US 7,042,487 B2
(45) Date of Patent: May 9, 2006

(54) IMAGING ELEMENT FOR ELECTRONIC ENDOSCOPES AND ELECTRONIC ENDOSCOPE EQUIPPED WITH THE IMAGING ELEMENT

(75) Inventor: Masaaki Nakashima, Saitama (JP)

(73) Assignee: PENTAX Corporation, Tokyo (JP)

( * ) Notice: Subject to any disclaimer, the term of this patent is extended or adjusted under 35 U.S.C. 154(b) by 664 days.

(21) Appl. No.: 09/931,881

(22) Filed: Aug. 20, 2001

(65) Prior Publication Data
US 2002/0021356 A1   Feb. 21, 2002

(30) Foreign Application Priority Data
Aug. 21, 2000   (JP) .............................. 2000-250206

(51) Int. Cl.
*A62B 1/04* (2006.01)

(52) U.S. Cl. .......................... 348/65; 348/76; 348/77; 348/230; 600/160; 600/109; 600/114

(58) Field of Classification Search ................. 348/65, 348/68, 70, 230, 76, 77; 600/101, 109, 114, 600/160
See application file for complete search history.

(56) References Cited

U.S. PATENT DOCUMENTS

| 4,489,350 | A  | * | 12/1984 | Kimura .................... 348/230.1 |
| 5,408,265 | A  | * | 4/1995  | Sasaki ......................... 348/70 |
| 5,427,087 | A  |   | 6/1995  | Ito et al. |
| 5,776,049 | A  | * | 7/1998  | Takahashi .................... 600/111 |
| 6,438,302 | B1 | * | 8/2002  | Utsui et al. ................. 385/117 |
| 6,476,851 | B1 | * | 11/2002 | Nakamura .................... 348/65 |

* cited by examiner

*Primary Examiner*—Shawn S. An
(74) *Attorney, Agent, or Firm*—Greenblum & Bernstein, P.L.C.

(57) ABSTRACT

An imaging element for an electronic endoscope is disclosed. The electronic endoscope has an elongated tubular main body. At the tip end portion of the main body, there are provided an optical imaging system comprising a convex lens, a concave lens and an optical low-pass filter, a CMOS type imaging element having a CMOS sensor, and a pair of light distribution lenses. The imaging element includes the CMOS sensor, a signal processing circuit for processing a signal outputted from the CMOS sensor, and a signal control circuit for timing control for extracting a signal from the CMOS sensor. In this imaging element, the signal processing circuit and the signal control circuit are arranged along the periphery of the light-receiving surface of the CMOS sensor so that a center of the base of the sensor on the light-receiving surface is substantially aligned with a center of an effective imaging region of the image sensor.

17 Claims, 10 Drawing Sheets

IMAGING ELEMENT FOR ELECTRONIC ENDOSCOPES AND ELECTRONIC ENDOSCOPE EQUIPPED WITH THE IMAGING ELEMENT

BACKGROUND OF THE INVENTION

1. Field of the Invention

The present invention relates to an imaging element for electronic endoscopes and an electronic endoscope equipped with the imaging element.

2. Description of the Related Art

In the field of medicine, electronic endoscope systems are used as diagnostic systems for examining internal sites of the human body.

In general, such an electronic endoscope system includes a light source device and an endoscope which is removably mounted (connected) to the light source device. The end scope is provided with a CCD imaging sensor (imaging element) and an imaging optical system which are provided at the tip end portion thereof.

As the imaging element, an imaging element is equipped with a CMOS (Complementary Metal Oxide Semiconductor) sensor (hereinafter, referred to as "CMOS type imaging element") attracts attention.

This CMOS type imaging element has various advantages. For example, in the case of the CMOS type imaging element, a CMOS sensor and its circumference circuits can be formed on the single substrate (on the same chip) according to the general MOS manufacturing process.

Figure 10:
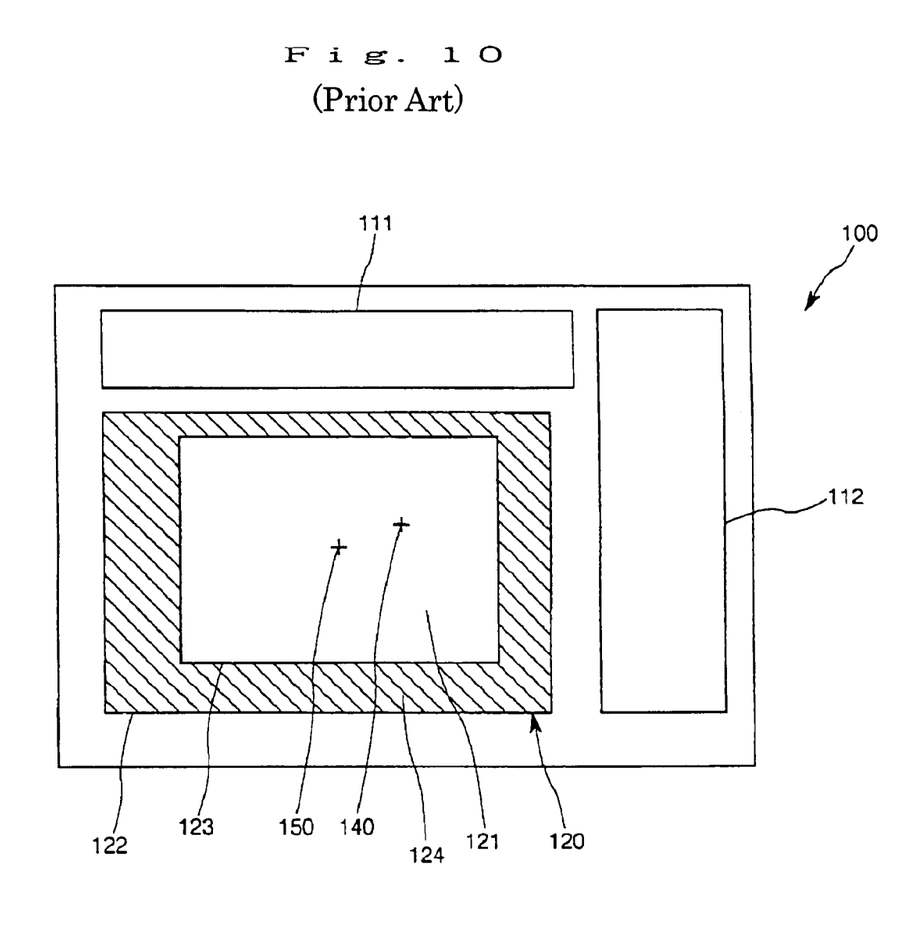
FIG. 10 is a schematic view which shows the imaging element used in the conventional electronic endoscope.

FIG. 10 is a plane view showing the imaging element used in the conventional electronic endoscopes.

The imaging element 100 shown in this figure is a CMOS type imaging element, which comprises a CMOS sensor 120, a control circuit 111 which performs timing control, and a signal processing circuit 112 which performs signal processing. The control circuit 111 is arranged at the upper side of the CMOS sensor 120 in FIG. 10, and the signal processing circuit 112 is arranged at the right side of the CMOS sensor 120 in FIG. 10.

The CMOS sensor 120 includes an imaging region 122. The imaging region 122 is composed of an effective imaging region 123 and a shading region 124 which is provided around the periphery of the effective imaging region 123. This shading region 124 (shown by the slanting lines in FIG. 10) is provided for detecting are ference level of optical black. The shading region 124 is normally referred to as an "optical black (optical black portion)."

In such an imaging element 100, as shown in FIG. 10, the center 150 of the effective region 123 of the imaging region 122 is not aligned with (coincided with) the center 140 of the imaging element 100 on a light-receiving surface 121.

The imaging element 100 and the imaging optical system are provided inside a predetermined opening portion in the tip portion of the endoscope. However, as described above, the center 150 of the effective region 123 is displaced from the center 140 of the imaging element 100. Therefore, if the imaging element 100 is mounted in the opening portion without any adjustment, the center of the imaging optical system (i.e., the intersection point between the optical axis of the imaging optical system and the light-receiving surface 121) is not aligned with the center 150 of the effective region 123.

For this reason, when the imaging element 100 is inserted into such an opening portion during assembly of the electronic endoscope, a centering adjustment (that is, an adjustment for correcting eccentricity) is carried out.

This centering adjustment is carried out by providing an adjustment spacer (centering means, not shown) outside the imaging element 100 using a predetermined jig so that the center 140 of the imaging element 100 containing the spacer is aligned with the center 150 of the effective region 123.

However, such centering adjustment operations are difficult to carry out automatically, and therefore a significant amount of time and labor is required for assembling the electronic endoscope.

Further, because the spacer has to be provided outside the imaging element 100, the additional space for housing such spacer is needed inside the tip portion of the electronic endoscope, which results in a problem in that the diameter of the electronic endoscope is enlarged to such an extent.

SUMMARY OF THE INVENTION

Therefore, it is an object of the present invention to provide an imaging element for electronic endoscopes of which positioning operation can be easily and reliably carried out and which makes it possible to reduce the diameter of the electronic endoscope.

In order to achieve the object, the present invention is directed to an imaging element for an electronic endoscope, which comprises a base; an image sensor mounted on the base, the imaging sensor having a light-receiving surface and an effective imaging region; and a predetermined circuit mounted on the base for taking out a signal from the image sensor, wherein the predetermined circuit is arranged along the periphery of the light-receiving surface of the image sensor on the base so that a center of the base on the light-receiving surface of the image sensor is substantially aligned with a center of the effective imaging region of the image sensor.

By using the imaging element having the structure described above, it becomes possible to position the imaging element with respect to an imaging optical system without providing any adjustment spacer (centering means) outside the imaging element (i.e., between the imaging element and the frame member). In other words, it becomes possible to align the center of the imaging optical system (i.e., the center of the base or the intersection point between the optical axis O of the imaging optical system and the light-receiving surface) with the center of the effective region without providing any adjustment spacer. Therefore, the diameter of the main body of an endoscope can be made small, and the number of parts can be reduced.

Further, when this invention is applied to the main body of an endoscope for medical use, the reduced diameter of the main body of the endoscope makes it possible to reduce the burden of a patient. Furthermore, since it is not necessary to perform eccentric adjustment (alignment adjustment) during the assembly process of the main body of the endoscope, the assembly of the main body of the endoscope can be carried out easily and quickly as compared with the case where such eccentric adjustment is performed.

In the present invention, it is preferred that the base has an outer profile of a substantially rectangular shape, and the effective imaging region is also formed into a substantially rectangular shape, in which the effective imaging region is arranged with respect to the base so that one side of the effective imaging region is substantially in parallel with the corresponding side of the base.

Further, it is also preferred that the predetermined circuit includes a signal processing circuit for carrying out signal processing of a signal outputted from the image sensor, and a control circuit for carrying out timing control to extract a signal from the image sensor.

In one embodiment, the signal processing circuit includes an A/D converter which converts an analog signal from the image sensor into a digital signal. In this case, it is preferred that the signal processing circuit includes a circuit which generates a video signal.

In other embodiment, the signal processing circuit includes an A/D converter which converts an analog signal from the image sensor into a digital signal, a circuit which generates a digital video signal based on the signal from the A/D converter, and a D/A converter which converts the digital signal from the generation circuit into an analog signal.

Furthermore, in the present invention, it is preferred that the image sensor is a CMOS sensor, and the control circuit has a circuit which specifies an address of a horizontal scanning direction of the image sensor and a circuit which specifies an address of a vertical scanning direction of the image sensor.

Moreover, it is also preferred that the signal processing circuit is arranged in a substantially L-shaped area along with two continuous sides of the base, and the control circuit is arranged in a substantially L-shaped area along with the other two continuous sides of the base. This arrangement is particularly preferred for achieving the object of the present invention.

The other aspect of the present invention is directed to an electronic endoscope which comprises an elongated flexible endoscope main body having a tip portion, the tip portion of the main body being adapted to be inserted into an object to be observed; and an imaging element provided in the tip part of the main body for taking an image of a part to be observed of the object. The imaging element comprises a base; an image sensor mounted on the base, the imaging sensor having a light-receiving surface and an effective imaging region; and a predetermined circuit mounted on the base for taking out a signal from the image sensor, wherein the predetermined circuit is arranged along the periphery of the light-receiving surface of the image sensor on the base so that a center of the base on the light-receiving surface of the image sensor is substantially aligned with a center of the effective imaging region of the image sensor.

In the present invention, it is preferred that the base has an outer profile of a substantially rectangular shape, and the effective imaging region is also formed into a substantially rectangular shape, in which the effective imaging region is arranged with respect to the base so that one side of the effective imaging region is substantially in parallel with the corresponding side of the base.

Further, it is also preferred that the predetermined circuit includes a signal processing circuit for carrying out signal processing of a signal outputted from the image sensor, and a control circuit for carrying out timing control to extract a signal from the image sensor.

In one embodiment, the signal processing circuit includes an A/D converter which converts an analog signal from the image sensor into a digital signal. In this case, it is preferred that the signal processing circuit includes a circuit which generates a video signal.

In other embodiment, the signal processing circuit includes an A/D converter which converts an analog signal from the image sensor into a digital signal, a circuit which generates a digital video signal based on the signal from the A/D converter, and a D/A converter which converts the digital signal from the generation circuit into an analog signal.

Furthermore, in the present invention, it is preferred that the image sensor is a CMOS sensor, and the control circuit has a circuit which specifies an address of a horizontal scanning direction of the image sensor and a circuit which specifies an address of a vertical scanning direction of the image sensor.

Moreover, it is also preferred that the signal processing circuit is arranged in a substantially L-shaped area along with two continuous sides of the base, and the control circuit is arranged in a substantially L-shaped area along with the other two continuous sides of the base.

Furthermore, preferably, the electronic endoscope further comprises an imaging optical system for forming an image of the observation part on the light receiving surface of the imaging sensor, and an opening portion provided in the tip portion of the main body for receiving the imaging optical system and the imaging element, in which the imaging optical system and the imaging element are disposed within the opening portion so that the optical axis of the imaging optical system passes through the center of the base of the imaging element.

These and other objects, structures and results of the present invention will be apparent more clearly when the following detailed description of the preferred embodiments is considered taken in conjunction with the accompanying drawings.

DETAILED DESCRIPTION OF THE PREFERRED EMBODIMENTS

A detailed description of the preferred embodiments of an imaging element for electronic endoscopes and an electronic endoscope equipped with the imaging element according to the present invention will now be given below with reference to the appended drawings.

Figure 1:
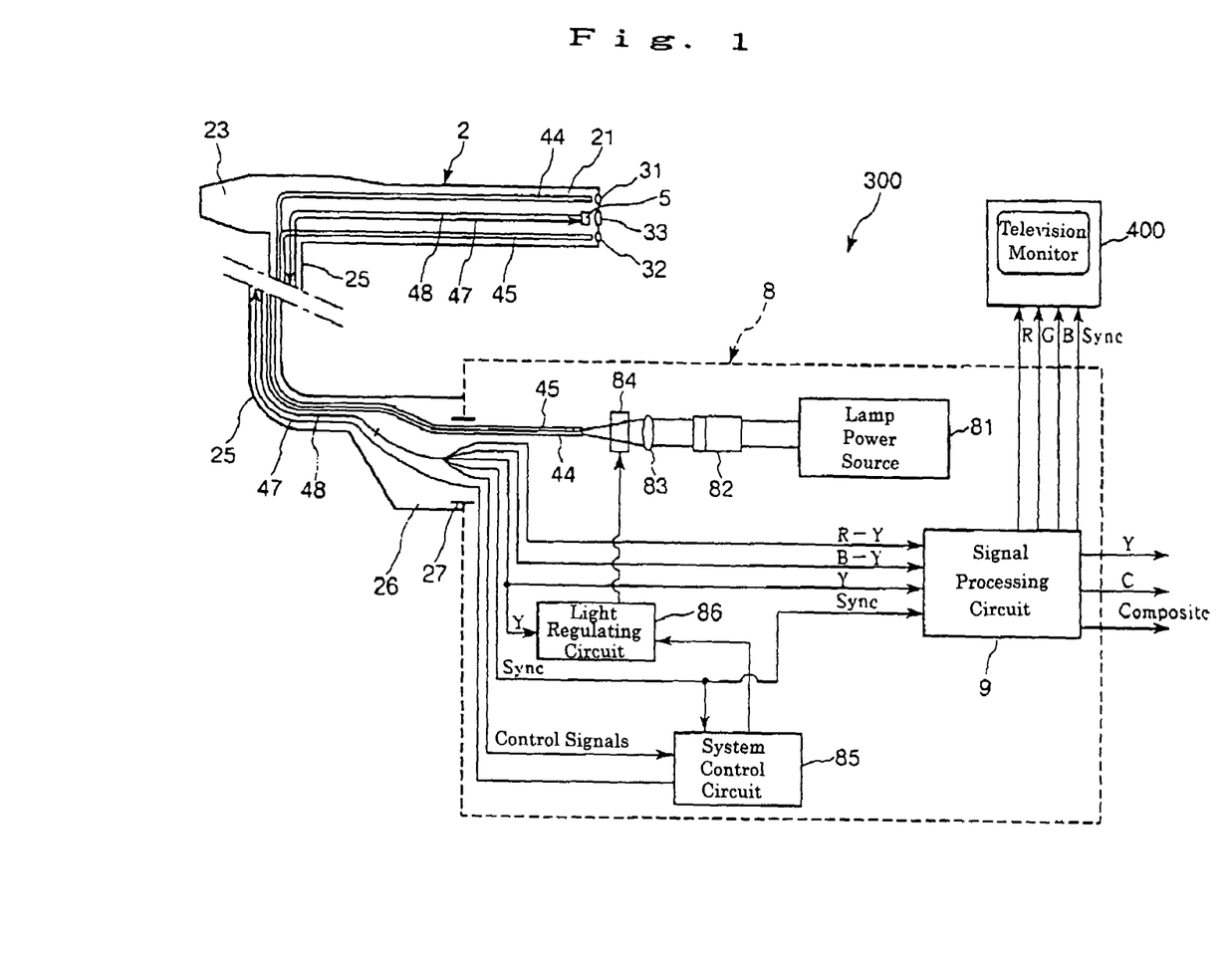
FIG. 1 is a block diagram which generally shows an electronic endoscope system provided with an electronic endoscope having an imaging element of a first embodiment according to the present invention and a light source device connected to the electronic endoscope.
Figure 2:
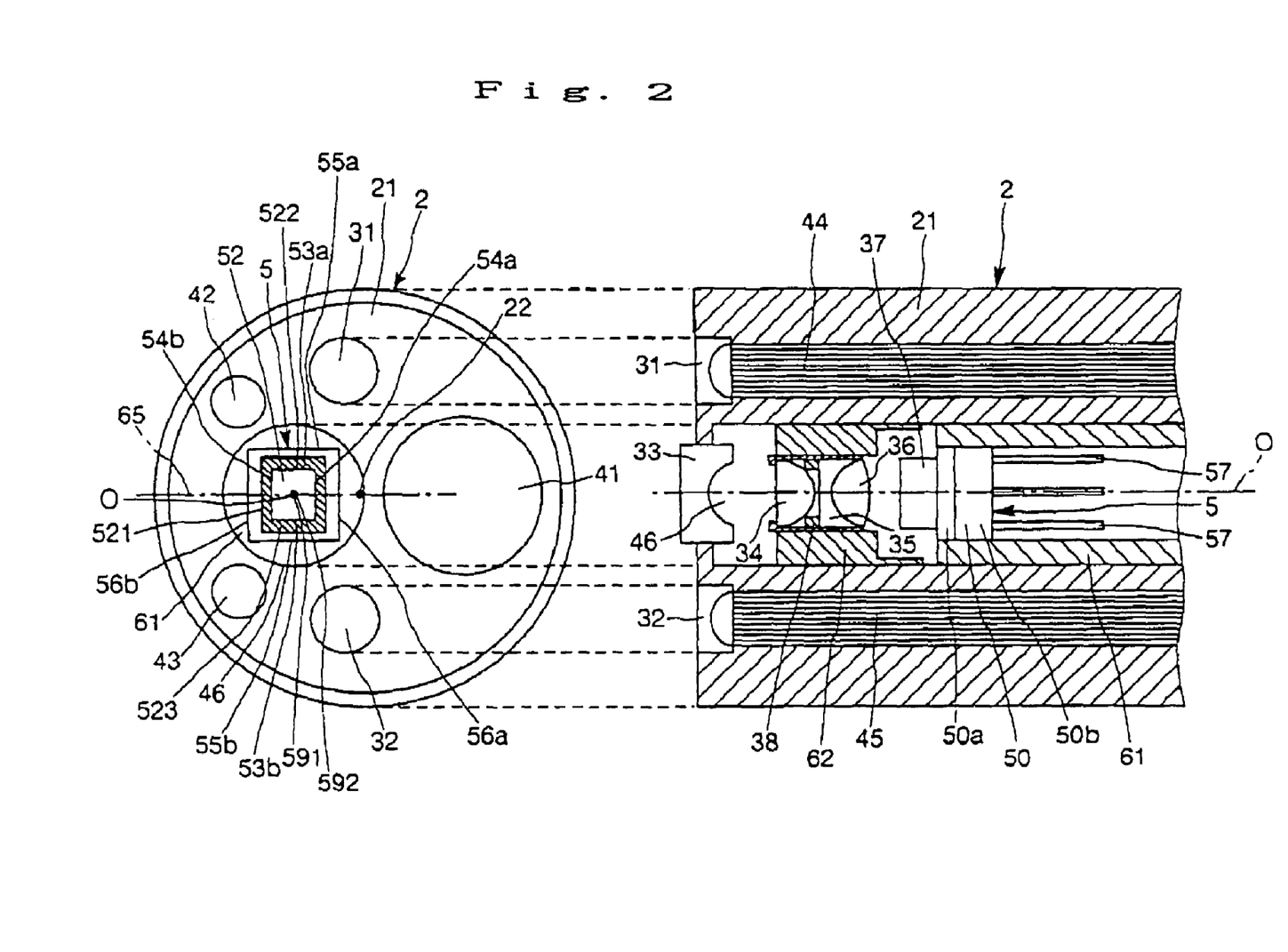
FIG. 2 is a diagram (including a bottom view and a cross-sectional view) of the tip portion of the electronic endoscope shown in FIG. 1.
Figure 3:
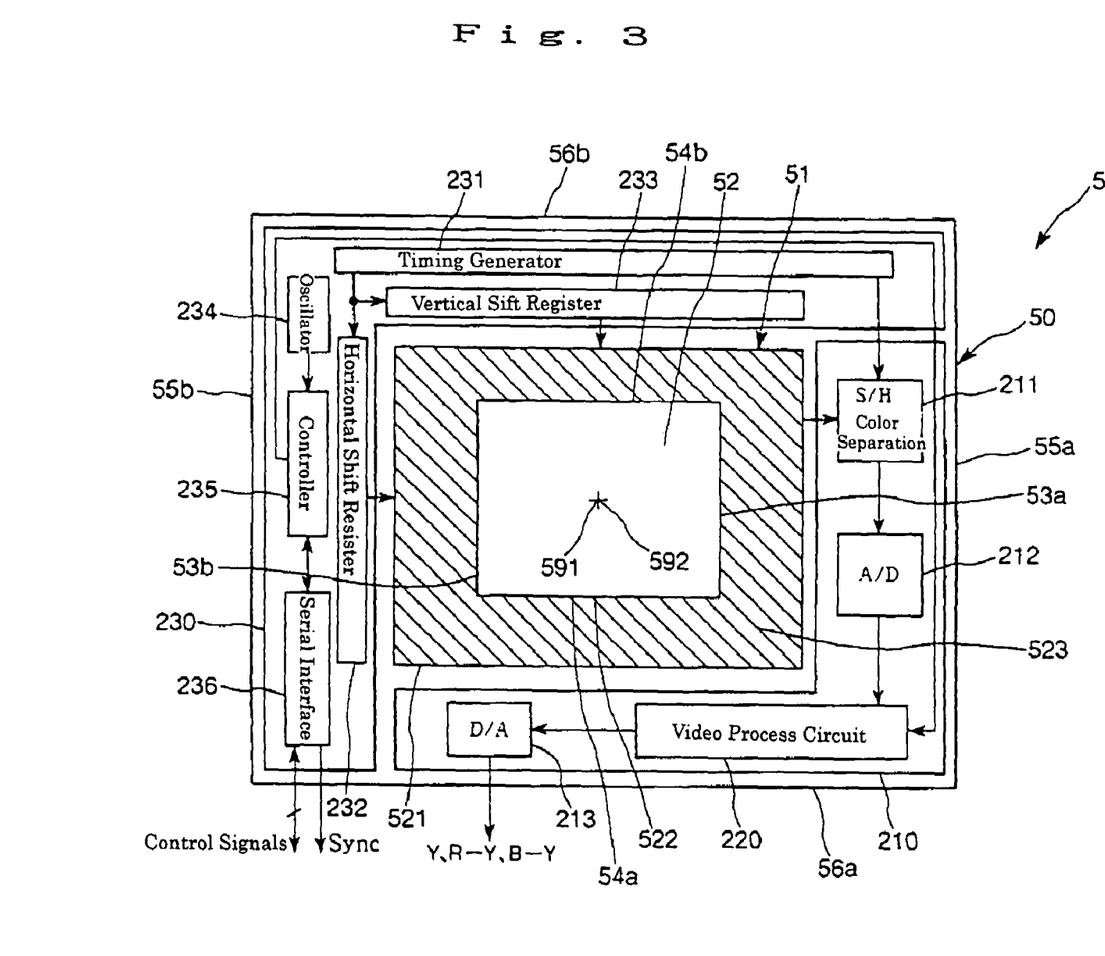
FIG. 3 is a plan view which schematically shows the structure of the first embodiment of the imaging element according to the present invention.
Figure 4:
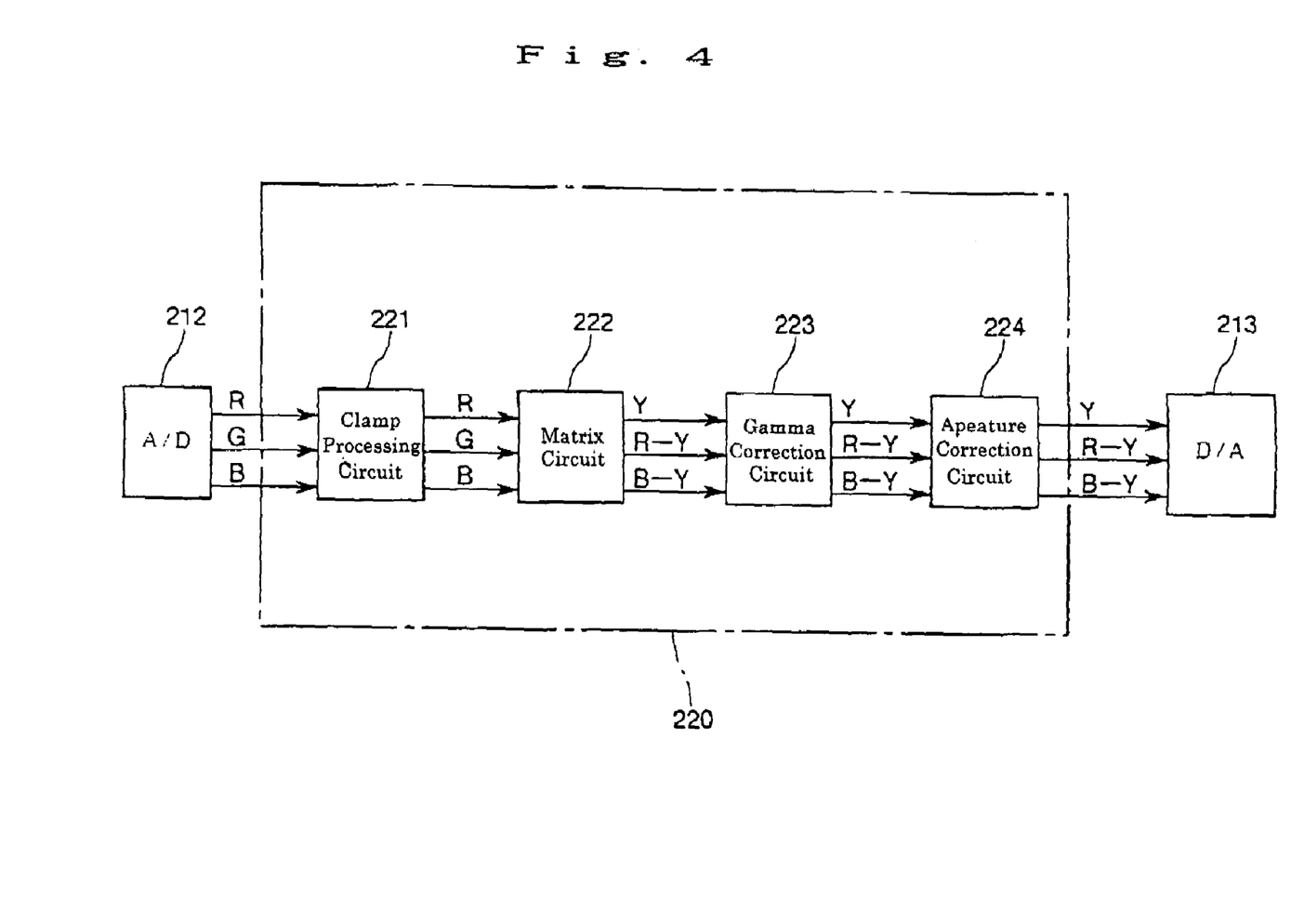
FIG. 4 is a block diagram of the video process circuit of the imaging element shown in FIG. 3.
Figure 5:
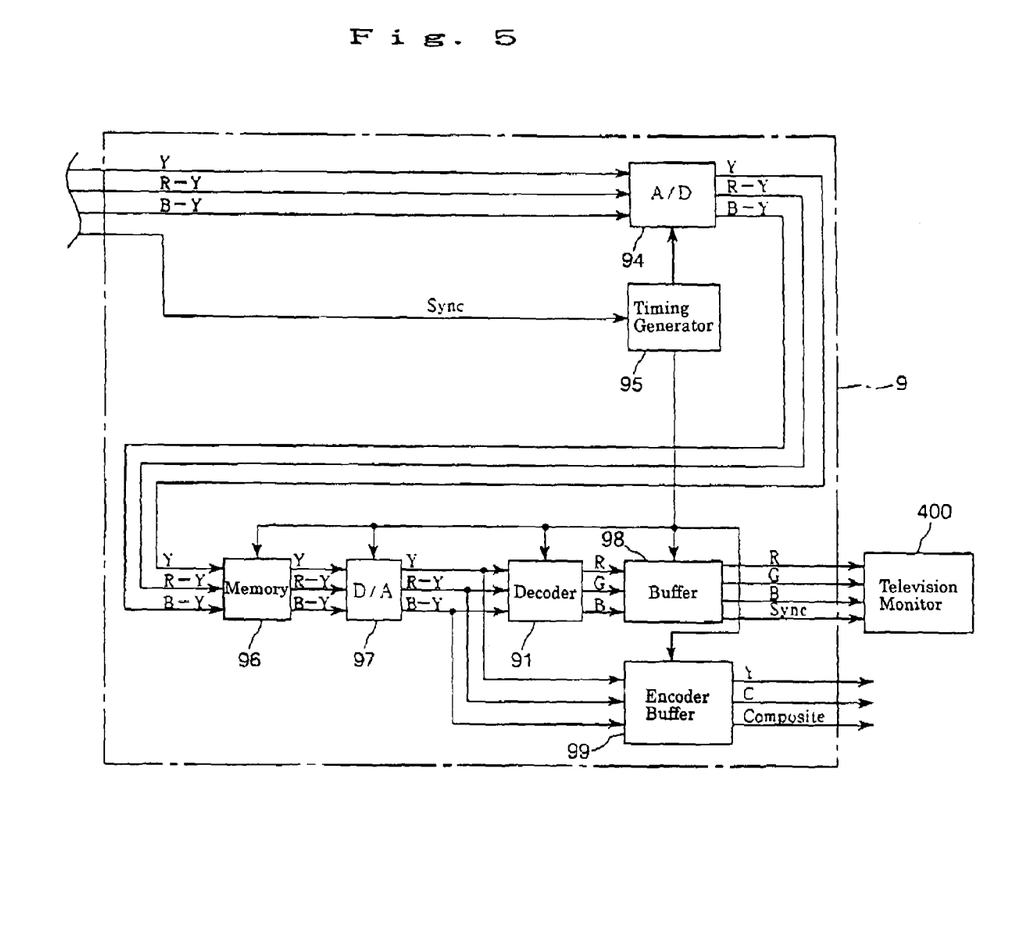
FIG. 5 is a block diagram of the signal processing circuit of the light source device for the electronic endoscope system shown in FIG. 1.

FIG. 1 is a block diagram which generally shows an electronic endoscope system provided with an electronic endoscope having an imaging element of a first embodiment according to the present invention and a light source device connected to the electronic endoscope; FIG. 2 is a diagram (including a bottom view and a cross-sectional view) of the tip portion of the electronic endoscope shown in FIG. 1; FIG. 3 is a plan view which schematically shows the structure of the first embodiment of the imaging element according to the present invention; FIG. 4 is a block diagram of the video process circuit of the imaging element shown in FIG. 3; and FIG. 5 is a block diagram of the signal processing circuit of the light source device for the electronic endoscope system shown in FIG. 1. In connection with these drawings, however, it is to be noted that the bottom view of FIG. 2 does not show the imaging optical system, and a part of signal lines is omitted in each figure showing the circuit configuration.

In addition, it is also to be noted that in the following description, the right-and-left direction in the sectional view of FIG. 2 is referred to as "the optical axis direction of an imaging optical system", the left-hand side in the sectional view of FIG. 2 is referred to as "tip or tip side" of the electronic endoscope, and the right-hand side in the sectional view of FIG. 2 is referred to as "base or base end side" of the electronic endoscope.

As shown in FIG. 1, an electronic endoscope system (endoscope system) 300 includes a light source device 8 and an electronic endoscope 1 which is removably connected to the light source device 8. Hereinafter, the electronic endoscope is simply referred to as an "endoscope."

The endoscope 1 is equipped with an endoscope main body 2 which is formed into an elongated flexible (elastic) tubular body (hereinafter, simply referred to as "main body").

The main body 2 includes an operation section 23 provided at the base end portion thereof, and a plurality of function channels provided inside the main body 2 along the lengthwise direction thereof. As shown in FIG. 2, the function channels include a forceps channel (lumen) 41 through which forceps and treatment instruments such as medical laser instruments are to be passed, a water supplying channel 42, and an air supplying channel 43. In addition, there are provided another two passages for accommodating light guide optical fiber bundles (light cable bundles) 44 and 45.

Further, as shown in FIG. 2, a pair of light distribution lenses (illumination lenses) 31 and 32 are provided in the tip of the main body 2. These light distribution lenses 31 and 32 are provided at the tips of the light guide optical fiber bundles 44 and 45, respectively.

Further, an opening portion (bore) 46 is formed in the main body 2 along the lengthwise direction thereof. As shown in FIG. 2, the opening portion 46 is arranged at an eccentric position away from the central axis (axis line) 22 of the main body 2.

Also, inside the opening portion 46 in the tip portion 21 of the main body 2, there are provided an imaging optical system which is comprised of an objective lens 33, a convex lens 34, a concave lens 35, a convex lens 36 and an optical low pass filter 37, and an imaging element 5. They are arranged in this order from the tip (i.e., the left side in FIG. 2) toward the base (i.e., the right side in FIG. 2). In this arrangement, the optical low-path filter 37 is concentrically installed on the cover 50a of the imaging element 5 (which will be described later).

The imaging element 5 is a CMOS type imaging element equipped with a CMOS (Complementary Metal Oxide Semiconductor) sensor 51. This imaging element 5 is supported by a frame member 61, and the imaging element 5 is inserted into the opening portion 46 together with the frame member 61. The frame member 61 has a cylindrical shape with a hollow spacing formed in the center thereof, in which the hollow spacing has a square shape in cross section. The structure of the imaging element 5 will be described later in more detail.

Further, the convex lenses 34, 36 and the concave lens 35 are supported by a lens support (lens holder) 62, and these lenses are inserted together with the lens support 62 into the opening portion 46. The lens support 62 has a cylindrical shape with a hollow spacing formed in the center thereof. Furthermore, a spacing ring 38 is arranged between the convex lens 34 and the concave lens 35.

Further, the objective lens 33 is provided in the central portion of the opening portion 46 at the tip of the main body 2, namely, at the tip side of the opening portion 46.

Also, all of the optical axes of the convex lenses 34, 36 and the concave lens 35 supported by the lens support 62 are aligned with the central axis of the lens support 62, and the optical axis of the objective lens 33 is aligned with the central axis of the lens support 62 when the lens support 62 is in an inserted state inside the opening portion 46. Namely, the endoscope 1 is designed so that the optical axes of the objective lens 33, the convex lenses 34, 36 and the concave lens 35 are all aligned with each other.

Furthermore, when the imaging element 5 is in a supported state in the frame member 61, the center 592 of an effective imaging region 522 (which will be described below) is aligned with the central axis of the frame member 61 on a light receiving surface 52 of the imaging element 5.

Accordingly, as shown in FIG. 2, when the frame member 61 and the lens support 62 are in an inserted state inside the opening portion 46, the central axis of the frame member 61 is aligned with the central axis of the lens support 62, and the optical axis O of the imaging optical system passes through the center 592 of the effective region 522 on the light-receiving surface 52 of the imaging element 5.

As shown in FIGS. 2 and 3, the imaging element 5 includes a housing (base) 50 having a rectangular parallelepiped shape. The housing 50 includes a base portion 50b and a transparent (light permeable) cover 50a which is attached to the base portion 50b. Here, the center 591 of the housing (base) 50 is the center of the imaging element 5.

The profile of the imaging element 5 in the plan view, namely the outer profile of the imaging element 5 when viewed from a perpendicular direction (the optical axis direction of the imaging optical system) to the light-receiving surface 52 has a rectangular shape, as shown in FIG. 3.

Housed inside the housing 50 is a CMOS sensor (image sensor) 51 which includes a rectangular imaging region 521.

The shading region (shown by the slanting line in FIG. 3) 523 for optically detecting a reference black level is arranged along the periphery of the imaging region 521 of the CMOS sensor 51. This shading region 523 is usually called as "optical black (optical black portion)."

In the imaging regions 521, the portion except this shading region 523 serves as an effective imaging region 522. This effective imaging region 522 also has a rectangular form.

One short side 55a of the housing 50 and the corresponding short side 53a of the effective imaging region 522 of the CMOS sensor 51 (which is parallel to the vertical scanning direction) are substantially parallel to each other, and another short side 55b of housing 50 and the corresponding another short side 53b of the effective imaging region 522 (which is parallel to the vertical scanning direction) are also substantially parallel to each other. With this result, one long side 56a of the housing 50 and the corresponding long side 54a of the effective imaging region 522 of the CMOS sensor 51 (which is parallel to the horizontal scanning direction) are substantially parallel to each other, and another long side 56b of the housing 50 and the corresponding another long side 54b of the effective imaging region 522 (which is parallel to the horizontal scanning direction) are also substantially parallel to each other.

In this imaging element 5, the CMOS sensor 51 and the circuits for taking out signals from the CMOS sensor 51 are arranged so that the center 591 of the housing (base) 50 on the light-receiving surface 52 and the center 592 of the effective imaging region 522 are substantially aligned with (coincided with) each other. These circuits include a signal processing circuit (circuits in a signal processing system) 210 which performs signal processing for the signals outputted from the CMOS sensor 51, and a control circuit (circuits in a signal control system) 230 which performs timing control for extracting the signal from the CMOS sensor 51.

Namely, the signal processing circuit 210 and the control circuit 230 are arranged around or along the periphery of the light-receiving surface 52 of the CMOS sensor 51 so that the center 591 of the housing (the base) 50 on the light-receiving surface 52 and the center 592 of the effective imaging region 522 are substantially aligned with each other. Specifically, the signal processing circuit 210 is arranged in a substantially L-shaped area along with the short side 55a and the long side 56a of the housing 50, and the control circuit 230 is arranged in a substantially L-shaped area along with the short side 55b and the long side 56b of the housing 50.

The signal processing circuit 210 of this imaging element 5 includes a sample hold color separation circuit 211, an A/D converter 212, a video process circuit 220 for generating a video signal, and a D/A converter 213. In this embodiment, the video signal includes a brightness signal (Y) and two color-difference signals (R-Y) and (B-Y).

As shown in FIG. 4, the video process circuit 220 includes a clamp processing circuit 221, a matrix circuit 222, a gamma correction circuit 223, and an aperture correction circuit 224.

Moreover, the control circuit 230 of the imaging element 5 includes a timing generator 231, a horizontal shift register 232 which specifies the address (pixel) of the horizontal scanning direction of the imaging element 5, a vertical shift register 233 which specifies the address (pixel) of the vertical scanning direction of the imaging element 5, an oscillator 234, a controller 235, and a serial interface 236.

Moreover, the imaging element 5 has several pins 57. FIG. 2 shows an example that the imaging element 5 has six pins 57.

As shown in FIG. 2, by using the imaging element 5 having the structure described above, it becomes possible to position the imaging element 5 with respect to the imaging optical system without providing any adjustment spacer (centering means) outside the imaging element 5 (i.e., between the imaging element 5 and the frame member 61). Namely, it becomes possible to align the center of the imaging optical system (i.e., the center 591 of the housing 50 or the intersection point between the optical axis O of the imaging optical system and the light-receiving surface 52) with the center 592 of the effective region 522 without providing any adjustment spacer.

In this way, because there is no need to provide any adjustment spacer (centering means), the number of components may be reduced.

Next, a description will be given for each of the function channels and the like arranged in the tip portion 21 of the main body 2.

As shown in FIG. 2, the imaging element 5 is arranged inside the opening portion 46 in such a way that a straight line (line segment) 65 which passes through the center 592 of the imaging region 522 and which is in parallel with the short sides 53a and 53b of the imaging region 522 passes through the central axis 22 of the main body 2. Further, as was described above, the objective lens 33, the convex lens 34, the concave lens 35, the convex lens 36 and the optical low pass filter 37 are respectively arranged in front of the imaging element 5.

The forceps channel 41 is arranged near the long side 56a of the imaging element 5 at an eccentric position away from the central axis 22.

The channels other than the forceps channel 41 are arranged symmetrically with respect to the straight line 65. Namely, the water supplying channel 42 and the light guide optical fiber bundle 44 are arranged near the short side 53a, and the air supplying channel 43 and the light guide optical fiber bundle 45 are arranged near the short side 53b, with the water supplying channel 42 and the air supplying channel 43 being positioned symmetrically with respect to the straight line 65, and the light guide optical fiber bundles 44 and 45 being positioned symmetrically with respect to the straight line 65. Further, as was described above, the light distribution lenses 31 and 32 are provided at the tips of the light guide optical fiber bundles 44 and 45, respectively.

By arranging each of the function channels in this way as described above, it becomes possible to further reduce the diameter of the main body 2.

As shown in FIG. 1, one end of a universal cord (cord-shaped coupling) 25 is connected to the base end portion of the main body 2.

The other end of the universal cord 25 is provided with a connecting portion 26 equipped with a connector 27. By means of the connector 27, the endoscope 1 is removably connected to the light source device 8 to establish an electrical and optical connection.

In addition, the connector 27 and the imaging element 5 are electrically connected through the signal lines 47 and 48.

Furthermore, the tip ends of the light guide optical fiber bundles 44 and 45 are positioned in contact with the light distribution lenses 31 and 32, and the base ends of the light guide optical fiber bundles 44 and 45 are connected to the connector 27.

As shown in FIG. 1, the light source device 8 includes a lamp power source 81, a light source lamp (light source) 82, a condenser lens 83, a diaphragm means 84, a system control circuit (control means) 85, a light regulating circuit 86, a signal processing circuit 9 and a casing (not shown in the drawing) which houses all of these components.

As shown in FIG. 5, the signal processing circuit 9 of the light source device 8 includes a decoder 91, an A/D converter 94, a timing generator 95, a memory 96, a D/A converter 97, a buffer 98 and an encoder buffer circuit 99.

Further, a television monitor (display means) 400 for displaying images of an observation part is removably connected to the light source device 8.

Next, the operation of the electronic endoscope system 300 will be described.

As shown in FIG. 1, when the power supply is turned on, electrical power is supplied from the lamp power source 81 to the light source lamp 82, and this causes illumination light to be emitted from the light source lamp 82 toward the light entrance end faces of the light guide optical fiber bundles 44 and 45.

Namely, the illumination light from the light source lamp 82 is first converged by the condenser lens 83, and then this converged illumination light passes through the diaphragm means 84 which regulates such illumination light to enable a predetermined amount of the illumination light to be incident on the light entrance end faces of the light guide optical fiber bundles 44 and 45. In this regard, the operation (control) of the diaphragm means 84 will be described later.

Then, such illumination light passes through the light guide optical fiber bundles 44 and 45, and then illuminates an observation part (i.e., the site of the body to be observed) via the light distribution lenses 31 and 32.

Next, the reflected light from the observation part is guided through the objective lens 33, the convex lens 34, the concave lens 35 and the convex lens 36 to form an image of the observation part on the light-receiving surface 52 of the imaging element 5 (see FIG. 2). At this time, the high frequency wave components of the reflected light are eliminated by the optical low pass filter 37 (see FIG. 2).

Further, a synchronizing signal (Sync) is generated in the timing generator 231 of the imaging element 5 shown in FIG. 3, and as shown in FIG. 1 and FIG. 5, this synchronizing signal (Sync) is inputted into both the system control circuit 85 and the timing generator 95 of the signal processing circuit 9 of the light source device 8, respectively.

Further, a sample hold signal (SHP) is generated in the timing generator 231, and this sample hold signal (SHP) is inputted into the sample-hold and color-separation circuit 211.

In an oscillator 234, a predetermined clock signal is generated and this clock signal is inputted into a controller 235.

Moreover, in the controller 235, each control signal such as an enhanced level signal, brightness control signal, and color balance signal is generated, and these control signals are then inputted into the system control circuit 85 shown in FIG. 1 through the video process circuit 220 and the serial interface 236.

In the system control circuit 85, for example, each control signal such as a signal for controlling the drive of the imaging element 5 is generated, and these control signals are then inputted into the controller 235 through the serial interface 236.

The controller 235 controls the drive of the horizontal shift register 232 and the vertical shift register 233 through the timing generator 231 based on the control signal from the system control circuit 85.

Based on the operations of these horizontal sift register 232 and vertical sift register 233, the pixel of the imaging element 5 is sequentially specified, and a pixel signal (electric charge signal) is outputted from the specified pixel. That is, an image of the observation part (an image of the observation part produced on the light receiving surface 52) is taken by driving the imaging element 5, and a pixel signal is outputted from each pixel of the imaging element 5.

As shown in FIG. 3, the pixel signals from the imaging element 5 are inputted into the sample-hold and color-separation circuit 71. The sample-hold and color-separation circuit 71 separates the pixel signals into the R (red), G (green) and B (blue) color signals, respectively, in accordance with the sample hold signals (SHP) from the timing generator 231.

Each of these R, G and B color signals is outputted from the sample hold color separation circuit 71, and then inputted into an A/D converter 212, respectively.

In the A/D converter 212, these R signal, G signal and B signal which have been supplied as analog signals are converted into digital signals.

As shown in FIG. 4, each of these R, G and B color signals is outputted from the A/D converter 212, and then inputted into a clamp processing circuit 221 of the video process circuit 220, respectively.

Further, in the timing generator 231, clamping pulse signals (Clamp) are generated in synchronization with the timing that the R, G and B signals from the pixels of the belt portion of the shading region 523, which is in the right or left side in FIG. 3, are inputted into the clamp processing circuit 221, and then thus generated clamping pulse signals are respectively inputted into the clamp processing circuit 221. In the clamp processing circuit 221, one clamping process is carried out in one horizontal scanning in synchronization with the clamp signal.

In this clamping process, each of the R, G and B signals is sampled in synchronization with the respective clamping pulse signal. Namely, by sampling each of the R, G and B signals from the pixels of the shading region 523, a reference level of the optical black is detected, and this detected reference level is held. Hereinafter, the reference level of optical black is simply referred to as a "reference level."

In the clamp processing circuit 221, a component for the reference level of the optical black is subtracted from each of the R, G and B signals from the pixels of the portion corresponding to the effective imaging region 522, so that proper R, G and B signals are obtained. In this way, it becomes possible to eliminate useless signal components (such as the dark current component and the like) from these signals, so that it becomes possible to obtain a proper image.

As shown in FIG. 4, each of the R, G and B signals is outputted from the clamp processing circuit 221, and then inputted into the matrix circuit 222, respectively. In the matrix circuit 222, two color-difference signals (R-Y, B-Y) and luminance signal (Y) are generated based on these input signals. The color-difference signal (R-Y), the color-difference signal (B-Y) and the luminance signal (Y) are then inputted into the D/A converter 213.

In the D/A converter 213, the color-difference signal (R-Y), the color-difference signal (B-Y) and the luminance signal (Y) which have been supplied as digital signals are converted into analog signals.

Then, the color-difference signal (R-Y), the color-difference signal (B-Y) and the luminance signal (Y) are outputted from the D/A converter 213, and then, as shown in FIG. 5, they are inputted into the A/D converter 94 of the signal processing circuit 9 of the light source device 8 of the endoscope.

Further, as shown in FIG. 1, each of the color-difference signal (R-Y), the color-difference signal (B-Y) and the luminance signal (Y) is also inputted into the light regulating circuit 86, and it is used in regulating the amount of illumination light in the diaphragm means 84. Namely, a reference voltage (Vref) for regulating the illumination light is inputted into the light regulating circuit 86 from the system control circuit 85, and based on this reference voltage (Vref) and the luminance signal (Y), the light regulating circuit 86 generates a control signal which is used to control the operation of the diaphragm means 84.

As shown in FIG. 5, in the A/D converter 94, the color-difference signal (R-Y), the color-difference signal (B-Y) and the luminance signal (Y) which have been supplied as analog signals are converted into digital signals.

Then, the color-difference signal (R-Y), the color-difference signal (B-Y) and the luminance signal (Y) are temporarily written into the memory 96. In this connection, using the data corresponding to the signals stored in the memory 96, it is possible to carry out, for example, a freeze processing to capture a desired still image.

Next, the color-difference signal (R-Y), the color-difference signal (B-Y) and the luminance signal (Y) are read out from the memory 96 and then inputted into the D/A converter 97.

In the D/A converter 97, the color-difference signal (R-Y), the color-difference signal (B-Y) and the luminance signal (Y) which have been supplied as digital signals are converted into analog signals. Then, the color-difference signal (R-Y), the color-difference signal (B-Y) and the luminance signal (Y) are inputted into both the decoder 91 and the encoder buffer circuit 99, respectively.

In the encoder buffer circuit 99, a luminance signal (Y), achroma signal (C) and a composite signal (Composite) are generated based on the color-difference signal (R-Y), the color-difference signal (B-Y) and the luminance signal (Y) from the D/A converter 97 and the synchronizing signal (Sync) from the timing generator 95, and then these luminance signal (Y), chroma signal (C) and composite signal (Composite) are outputted to an output terminal (not shown in the drawings).

Moreover, in the decoder 91, R signal, G signal and B signal are generated based on the color-difference signal (R-Y), the color-difference signal (B-Y), the luminance signal (Y) from the D/A converter 97 and the synchronized signal (Sync) from the timing generator 95.

Then, the R signal, G signal and B signals from the decoder 91, and the synchronized signal (Sync) from the timing generator 95 are inputted into the television monitor 400 through the buffer 98.

Then, a color image (electronic image) taken by the imaging element 5, namely, a color image in the form of motion picture is displayed on the television monitor 400.

As described above, according to the endoscope 1 having the imaging element 5 of the present invention, since the signal processing circuit 210 and the control circuit 230 are arranged so that they surround the periphery of the effective imaging region 524 of the CMOS sensor 51, it is possible to align the center 591 of the imaging element 5 with the center 592 of the effective region 524 of the imaging element 5 without carrying out any centering adjustment (i.e., an adjustment for correcting eccentricity). As a result, it is possible to reduce the number of assembly steps required for assembling the endoscope 1, and this results in improved productivity.

Further, in the present invention, there is no need to provide any adjustment spacer (centering means) outside the imaging element 5. Therefore, as compared with the case where such a spacer is required, it is possible to reduce the outer diameter of the frame member 61 (that is, the inner diameter of the opening portion 46), and this makes it possible to reduce the diameter of the main body 2 (in particular, the diameter of the tip portion 21 of the main body 2).

The reduced diameter of the endoscope 1 makes it possible to reduce the burden of a patient when it is used as an endoscope for medical fields.

Further, because there is no need to provide any adjustment spacer, the number of components can be reduced, and this makes it possible to lower production costs.

Furthermore, since the imaging element 5 is constructed from a CMOS type imaging element, it is possible to manufacture the imaging element 5 easily through a generally performed CMOS manufacturing process. Further, a CMOS sensor and its circumference circuits can be formed on the single substrate (the same chip). For these reasons, the number of the components can be decreased and therefore the manufacturing cost can also be reduced.

Moreover, power consumption can be also reduced as compared with the case where CCD (Charge Coupled Device) is used.

Moreover, since the imaging element 5 has the signal processing circuit 210 and the control circuit 230, it is possible to simplify the circuit configuration of the light source device 8 of the endoscope and the circuit configuration of the main body 2 of the endoscope 1.

Hereinbelow, the second embodiment of the imaging element for the electronic endoscopes of the present invention will be described.

Figure 7:
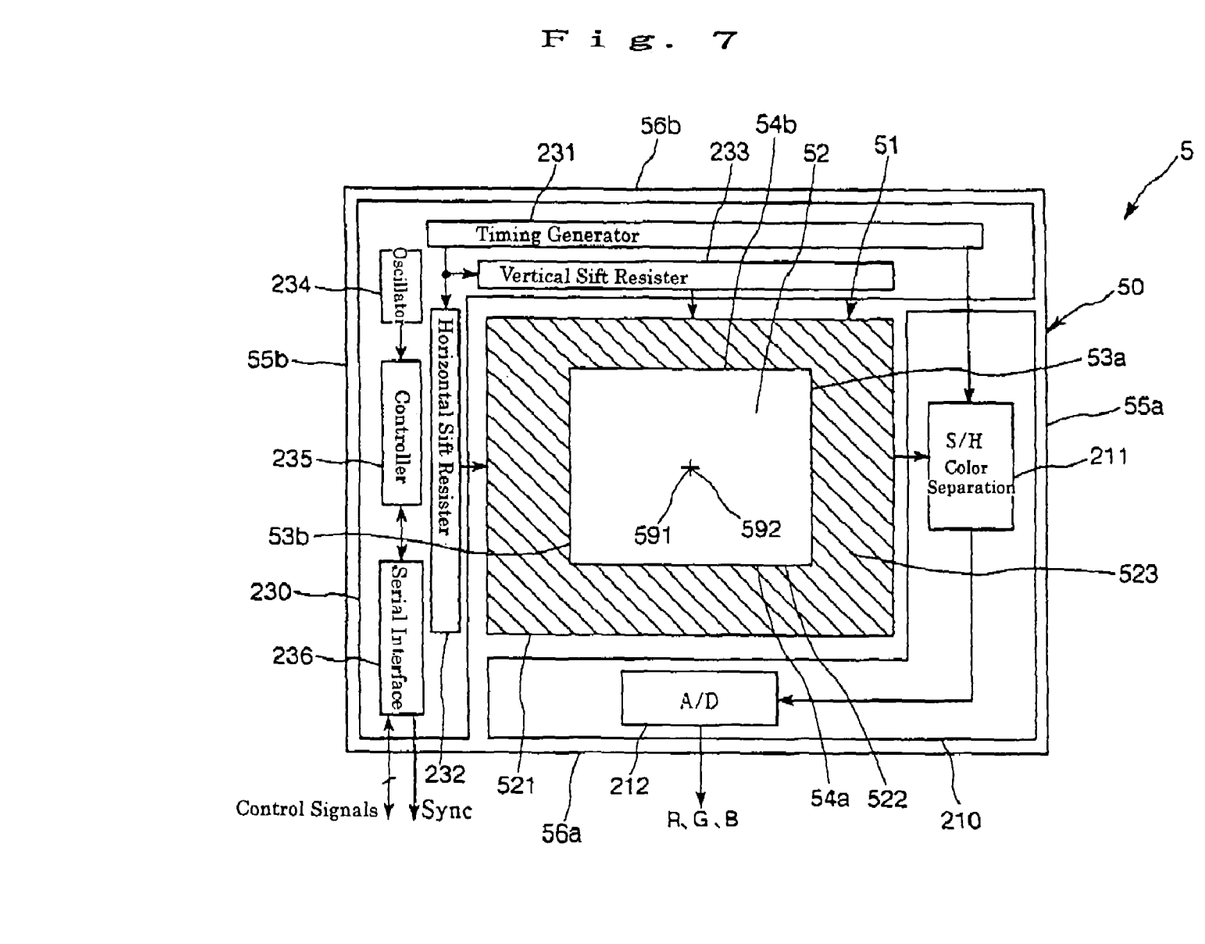
FIG. 7 is a plan view which schematically shows the structure of the second embodiment of the imaging element according to the present invention.

In the endoscope equipped with the imaging element of the second embodiment, the video process circuit 220 and the D/A converter 213, which are mounted in the housing 50 of the imaging element 5 of the first embodiment, are separated from the imaging element 5, and they are disposed in the connection part 26 near the light source device 8 of the endoscope.

In the following description, with regard to the common features with the first embodiment mentioned above, explanation is omitted, and only the main differences are explained.

Figure 6:
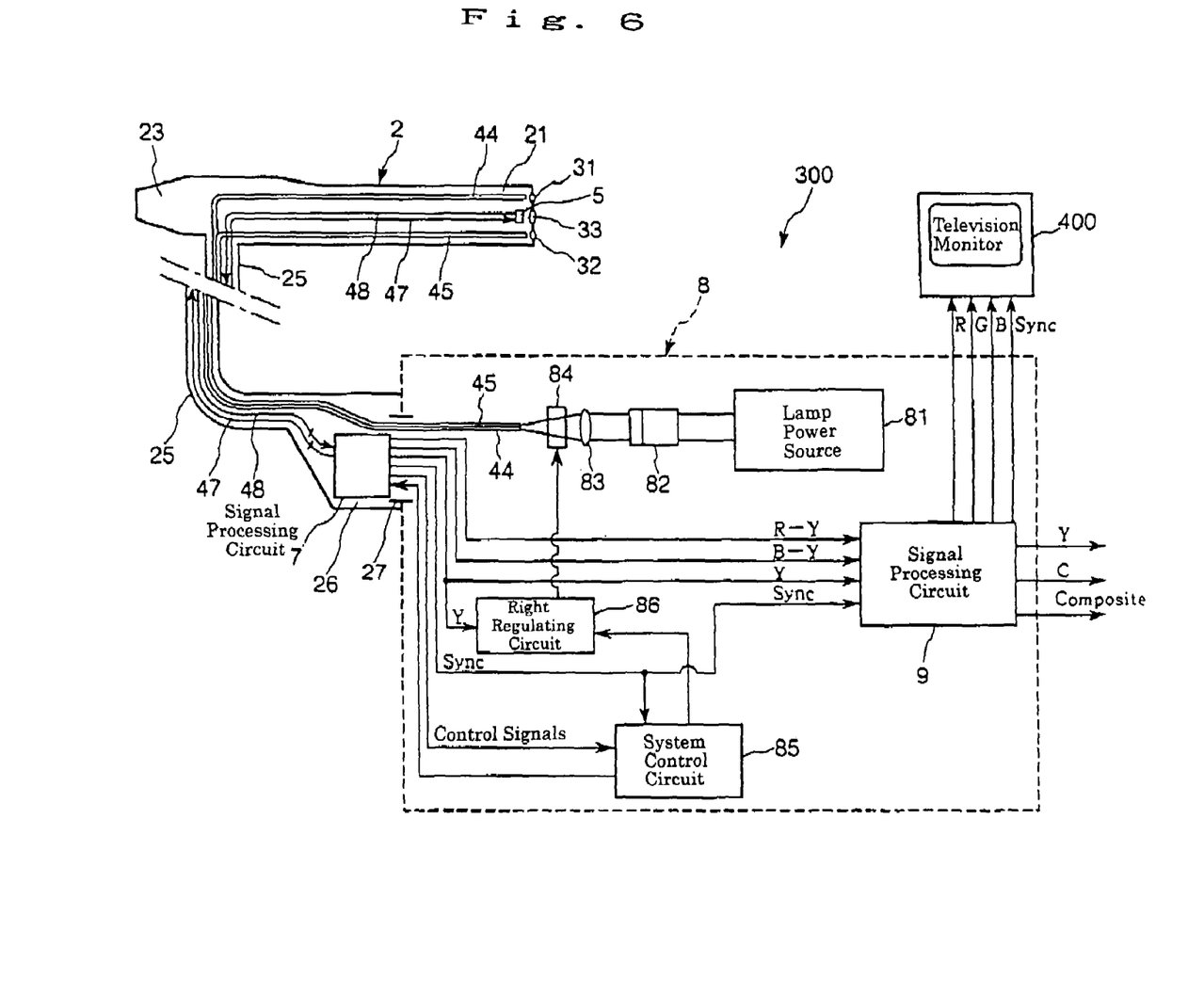
FIG. 6 is a block diagram which generally shows an electronic endoscope system provided with an electronic endoscope having an imaging element of a second embodiment according to the present invention and a light source device connected to the electronic endoscope.
Figure 8:
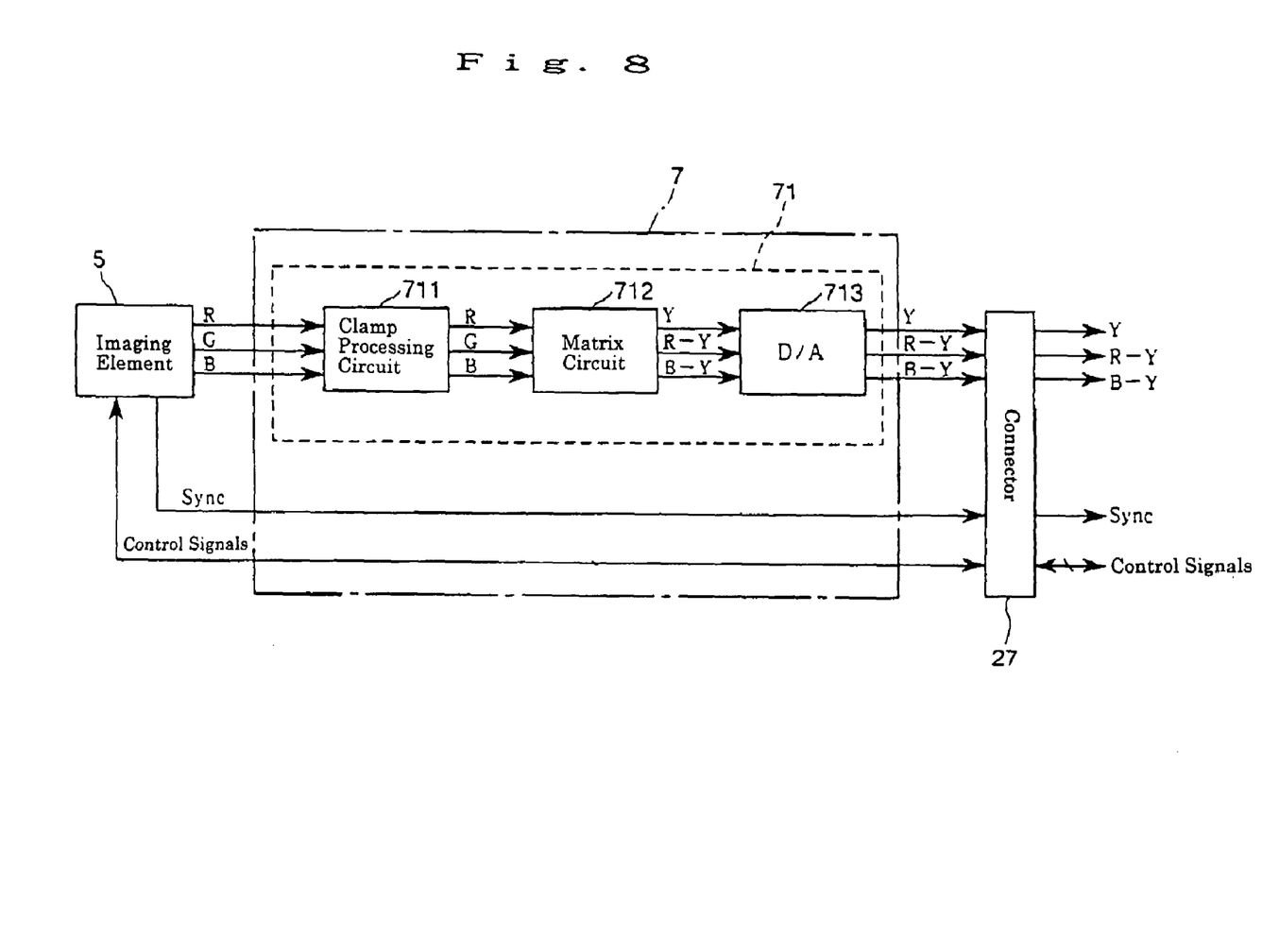
FIG. 8 is a block diagram of the signal processing circuit of the endoscope shown in FIG. 6.
Figure 9:
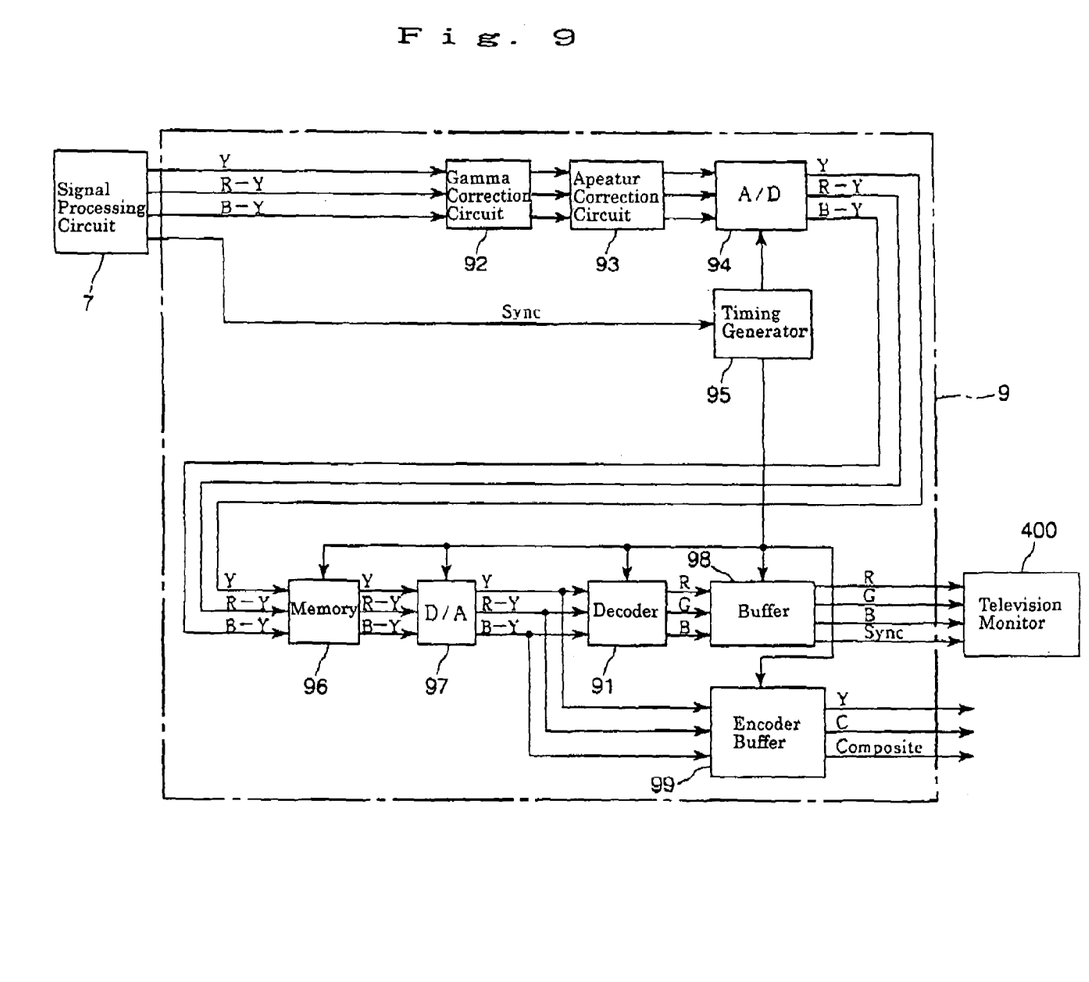
FIG. 9 is a block diagram of the signal processing circuit of the light source device of the electronic endoscope system shown in FIG. 6.

FIG. 6 is a block diagram which generally shows an electronic endoscope system provided with an electronic endoscope having an imaging element of the second embodiment according to the present invention and a light source device connected to the electronic endoscope; FIG. 7 is a plan view which schematically shows the structure of the second embodiment of the imaging element according to the present invention; FIG. 8 is a block diagram of the signal processing circuit of the endoscope shown in FIG. 6; and FIG. 9 is a block diagram of the signal processing circuit of the light source device of the electronic endoscope system shown in FIG. 6. In this connection, it is to be noted that a part of signal lines is omitted in each figure showing the circuit configuration.

As shown in FIG. 7, the signal processing circuit 210 of the imaging element 5 is composed of only the sample hold color separation circuit 211 and the A/D converter 212.

Further, as shown in FIG. 6 and FIG. 8, a signal processing circuit 7 which is electrically connected to the connector 27 is built in the connection part 26. The imaging element 5 is electrically connected to the signal processing circuit 7 through the signal lines 47 and 48.

As shown in FIG. 8, the signal processing circuit 7 includes a video process circuit 71 equipped with a clamp processing circuit 711, a matrix circuit 712 and a D/A converter 713.

Each of the R, G and B signals which have been outputted from the imaging element 5 is inputted into the video process circuit 71, respectively.

In the clamp processing circuit 711 of the video process circuit 71, a component for the reference level of the optical black is subtracted from each of the R, G and B signals from the pixels of the portion corresponding to the effective imaging region 522, so that proper R, G and B signals are obtained. In this way, it becomes possible to eliminate useless signal components (such as the dark current component and the like) from such signals, so that it becomes possible to obtain a proper image.

Then, each of the R, G and B signals is outputted from the clamp processing circuit 711, and then inputted into the matrix circuit 712, respectively.

In the matrix circuit 712, two color-difference signals (R-Y, B-Y) and luminance signal (Y) are generated based on these input signals. The color-difference signal (R-Y), the color-difference signal (B-Y) and the luminance signal (Y) are then inputted into a D/A converter 713.

In the D/A converter 713, the color-difference signal (R-Y), the color-difference signal (B-Y) and the luminance signal (Y) which have been supplied as digital signals are converted into analog signals.

Then, the color-difference signal (R-Y), the color-difference signal (B-Y) and the luminance signal (Y) are outputted from the video process circuit 71, and then, as shown in FIG. 6 and FIG. 9, they are inputted into the signal processing circuit 9 for the light source device 8 of the endoscope.

As shown in FIG. 9, the signal processing circuit 9 for the light source device 8 of the endoscope is comprised of a gamma correction circuit 92, an aperture correction circuit 93, an A/D converter 94, a timing generator 95, a memory 96, a D/A converter 97, a decoder 91, a buffer 98, and an encoder buffer 99.

Since the operations which will be made after this stage is the same as those performed in the first embodiment described above excepting that the color-difference signal (R-Y), the color-difference signal (B-Y) and the luminescence signal (Y) are corrected by the gamma correction circuit 92 and the aperture correction circuit 93, a detailed explanation thereof is omitted.

According to the endoscope equipped with the imaging element 5 of the second embodiment described above, the same advantages as those of the first embodiment mentioned above can be obtained.

In addition, since the imaging element 5 of this embodiment does not include the video process circuit 220 and the D/A converter 213 which are provided in the imaging element 5 in the first embodiment, the size of the outer periphery of the imaging element 5 can be made small, and, thereby, the diameter (that is, the diameter of the tip part 21) of the main body 2 of the endoscope can be made further small. Further, since the imaging element 5 of the second embodiment has the A/D converter 212 so as to output an signal in the form of a digital signal, quality of an image is not lowered by noise or the like even though the imaging element 5 is far from the signal processing circuit 7.

In the above, the imaging element for the electronic endoscopes of the present invention was explained based on the embodiments shown in the drawings. However, the present invention is not limited to these constructions, and it is possible to replace the components with arbitrary components having the same function.

For example, in this invention, the shape (form) of the imaging element, the shape of the imaging region, the shape of the effective imaging region, the shape of the shading region, the arrangement of the signal processing circuit, and the arrangement of the control circuit are not limited to those of the embodiments mentioned above.

Further, in the first and second embodiments of the present invention, the CMOS type imaging element is used since the circuit configuration can be designed easily and the circuits can be integrated. However, the imaging element of the present invention is not limited to such a CMOS type imaging element, and other types of imaging elements such as other MOS type imaging elements, CCD (Charge Coupled Device), and CPD and the like may be used, but CMOS type imaging element is most preferable in view of the advantages as described above.

Furthermore, in this invention, the imaging element may be either of the color imaging type or the monochrome imaging type.

Moreover, the imaging element for the electronic endoscopes of this invention is applicable to endoscopes for industrial use besides the endoscopes for medical use described above.

As described above, according to the imaging element for the electronic endoscopes of this invention, the circuits are arranged on the base so that the center of the base on the light-receiving surface and the center of the effective imaging region of the image sensor is substantially aligned with each other. Therefore, it is not necessary to provide any spacer (centering means) in the outside of the imaging element, and therefore the diameter of the main body of an endoscope can be made small, and the number of parts can be reduced.

Further, when this invention is applied to the main body of an endoscope for medical use, the reduced diameter of the main body of the endoscope makes it possible to reduce the burden of a patient.

Furthermore, since it is not necessary to perform eccentric adjustment (alignment adjustment) during the assembly process of the main body of the endoscope, the assembly of the main body of the endoscope can be carried out easily and quickly as compared with the case where such eccentric adjustment is performed.

Finally, it is to be understood that many changes and additions may be made to the embodiments described above without departing from the scope and spirit of the invention as defined in the following claims.

Further, it is also to be understood that the present disclosure relates to subject matter contained in Japanese Patent Application No. 2000-250206 (filed on Aug. 21, 2000) which is expressly incorporated herein by reference in its entirety.

What is claimed is:

1. An imaging element for an electronic endoscope, comprising:
   a base;
   an image sensor mounted on the base, the image sensor having a light-receiving surface and an effective imaging region; and
   a predetermined circuit mounted on the base for receiving a signal from the image sensor,
   wherein the predetermined circuit is arranged along the periphery of the light-receiving surface of the image sensor on the base so that a center of the base on the light-receiving surface of the image sensor is substantially aligned with a center of the effective imaging region of the image sensor.

2. The imaging element as claimed in claim 1, wherein the base has an outer profile of a substantially rectangular shape, and the effective imaging region also comprises a substantially rectangular shape, in which the effective imaging region is arranged with respect to the base so that one side of the effective imaging region is substantially parallel to the corresponding side of the base.

3. The imaging element as claimed in claim 1, wherein the predetermined circuit includes a signal processing circuit for carrying out signal processing of a signal outputted from the image sensor, and a control circuit for carrying out timing control to extract a signal from the image sensor.

4. The imaging element as claimed in claim 3, wherein the signal processing circuit includes an A/D converter which converts an analog signal from the image sensor into a digital signal.

5. The imaging element as claimed in claim 3, wherein the signal processing circuit includes a circuit which generates a video signal.

6. The electronic endoscope as claimed in claim 3, wherein the signal processing circuit includes an A/D converter which converts an analog signal from the image sensor into a digital signal, a circuit which generates a digital video signal based on the signal from the A/D converter, and a D/A converter which converts the digital signal from the generation circuit into an analog signal.

7. The electronic endoscope as claimed in claim 3, wherein the image sensor is a CMOS sensor, and the control circuit has a circuit which specifies an address of a horizontal scanning direction of the image sensor and a circuit which specifies an address of a vertical scanning direction of the image sensor.

8. The electronic endoscope as claimed in claim 3, wherein the signal processing circuit is arranged in a substantially L-shaped area along two adjacent sides of the base, and the control circuit is arranged in a substantially L-shaped area along the other two adjacent sides of the base.

9. An electronic endoscope, comprising:
an elongated flexible endoscope main body having a tip portion, the tip portion of the main body being adapted to be inserted into an object to be observed; and
an imaging element provided in the tip part of the main body for capturing an image of a part to be observed of the object, the imaging element comprising a base; an image sensor mounted on the base, the image sensor having a light-receiving surface and an effective imaging region; and
a predetermined circuit mounted on the base for receiving a signal from the image sensor, wherein the predetermined circuit is arranged along the periphery of the light-receiving surface of the image sensor so that a center of the base on the light-receiving surface of the image sensor is substantially aligned with a center of the effective imaging region of the image sensor.

10. The electronic endoscope as claimed in claim 9, wherein the base has an outer profile of a substantially rectangular shape, and the effective imaging region also comprises a substantially rectangular shape, in which the effective imaging region is arranged with respect to the base so that one side of the effective imaging region is substantially parallel to the corresponding side of the base.

11. The electronic endoscope as claimed in claim 9, wherein the predetermined circuit includes a signal processing circuit for carrying out signal processing of a signal outputted from the image sensor, and a control circuit for carrying out timing control to extract a signal from the image sensor.

12. The electronic endoscope as claimed in claim 11, wherein the signal processing circuit includes an A/D converter which converts an analog signal from the image sensor into a digital signal.

13. The electronic endoscope as claimed in claim 11, wherein the signal processing circuit further includes a circuit which generates a video signal.

14. The electronic endoscope as claimed in claim 11, wherein the signal processing circuit includes an A/D converter which converts an analog signal from the image sensor into a digital signal, a circuit which generates a digital video signal based on the signal from the A/D converter, and a D/A converter which converts the digital signal from the generation circuit into an analog signal.

15. The electronic endoscope as claimed in claim 11, wherein the image sensor is a CMOS sensor, and the control circuit has a circuit which specifies an address of a horizontal scanning direction of the image sensor and a circuit which specifies an address of a vertical scanning direction of the image sensor.

16. The electronic endoscope as claimed in claim 11, wherein the signal processing circuit is arranged in a substantially L-shaped area along two adjacent sides of the base, and the control circuit is arranged in a substantially L-shaped area along the other adjacent sides of the base.

17. The electronic endoscope as claimed in claim 9, further comprises an imaging optical system for forming an image of the observation part on the light receiving surface of the image sensor, and an opening portion provided in the tip portion of the main body for receiving the imaging optical system and the imaging element, in which the imaging optical system and the imaging element are disposed within the opening portion so that the optical axis of the imaging optical system passes through the center of the base of the imaging element.

* * * * *